US012246167B2

(12) United States Patent
McPherson et al.

(10) Patent No.: US 12,246,167 B2
(45) Date of Patent: Mar. 11, 2025

(54) AUTO-INJECTOR

(71) Applicant: Owen Mumford Limited, Woodstock (GB)

(72) Inventors: Paul McPherson, Woodstock (GB); Robert Bruns, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 1018 days.

(21) Appl. No.: 17/280,399

(22) PCT Filed: Sep. 26, 2019

(86) PCT No.: PCT/EP2019/076029
§ 371 (c)(1),
(2) Date: Mar. 26, 2021

(87) PCT Pub. No.: WO2020/064927
PCT Pub. Date: Apr. 2, 2020

(65) Prior Publication Data
US 2022/0111145 A1    Apr. 14, 2022

(30) Foreign Application Priority Data
Sep. 28, 2018 (GB) .................................... 1815829

(51) Int. Cl.
*A61M 5/20* (2006.01)
*A61M 5/32* (2006.01)

(52) U.S. Cl.
CPC ........ *A61M 5/2033* (2013.01); *A61M 5/3204* (2013.01); *A61M 2005/202* (2013.01);
(Continued)

(58) Field of Classification Search
CPC ........ A61M 5/20; A61M 5/2033; A61M 5/24; A61M 5/2422; A61M 5/28; A61M 5/3146;
(Continued)

(56) References Cited

U.S. PATENT DOCUMENTS

| 4,681,566 A | 7/1987 | Fenton |
| 2010/0137808 A1 | 6/2010 | Wilmot et al. |

(Continued)

FOREIGN PATENT DOCUMENTS

| EP | 2727617 A1 | 5/2014 |
| TW | 201818987 A | 6/2018 |
| WO | 2011012849 A1 | 2/2011 |

OTHER PUBLICATIONS

International Search Report and Written Opinion from corresponding International Application No. PCT/EP2019/076029, mailed Nov. 20, 2019 (12 pages).

(Continued)

*Primary Examiner* — Joel M Attey
*Assistant Examiner* — Alexandra Lalonde
(74) *Attorney, Agent, or Firm* — QUARLES & BRADY LLP (57) ABSTRACT

An auto-injector for receiving and operating a syringe. The auto-injector includes a housing for receiving the syringe, the housing comprising a main body and a hinged door operable into an open position and a closed position. The syringe is receivable within the housing when the hinged door is in the open position. At least one charging link is connected between the main body and the hinged door, wherein a connection of the at least one charging link to the main body and/or a connection of the at least one charging link to the hinged door is a slidable connection configured to slide on opening and closing of the hinged door and con-
(Continued)

figured to couple to at least one drive spring for priming of the at least one drive spring on the opening of the hinged door and/or the closing of the hinged door. The at least one drive spring is configured on activation of the auto-injector to drive a plunger driver forward within the auto-injector to operate the syringe received within the auto-injector.

19 Claims, 7 Drawing Sheets (52) U.S. Cl.
CPC ............... *A61M 2005/2026* (2013.01); *A61M 2005/206* (2013.01); *A61M 2005/2086* (2013.01)

(58) Field of Classification Search
CPC .......... A61M 5/31565; A61M 5/31571; A61M 5/3202; A61M 5/3204; A61M 5/3213; A61M 5/3243; A61M 5/3245; A61M 5/3257; A61M 5/326; A61M 5/3269; A61M 5/3271; A61M 5/3272; A61M 5/315; A61M 5/31501; A61M 5/31573; A61M 5/31575; A61M 5/31576; A61M 5/3159; A61M 5/32; A61M 5/3205; A61M 5/321; A61M 2005/2013; A61M 2005/2006; A61M 2005/202; A61M 2005/2026; A61M 2005/206; A61M 2005/2073; A61M 2005/208; A61M 2005/2086; A61M 2005/3265; A61M 2005/3254; A61M 2005/2403; A61M 2005/3143; A61M 2005/3261; A61M 2005/3267; A61M 2005/3268; A61M 2005/31508; A61M 2005/2414

See application file for complete search history.

(56) References Cited

U.S. PATENT DOCUMENTS

| | | | |
|---|---|---|---|
| 2011/0028910 A1 | 2/2011 | Weber | |
| 2013/0138049 A1* | 5/2013 | Kemp | A61M 5/322 604/197 |
| 2014/0336589 A1* | 11/2014 | Sund | A61M 5/2033 604/228 |
| 2015/0290392 A1 | 10/2015 | Henderson et al. | |
| 2015/0297833 A1* | 10/2015 | Henderson | A61M 5/3129 |
| 2016/0346476 A1 | 12/2016 | Cappello et al. | |

OTHER PUBLICATIONS

Combined Search and Examination Report from corresponding Great Britain Application No. GB1815829.5 dated Mar. 28, 2019 (7 pages).
International Preliminary Report on Patentability for corresponding PCT Application No. PCT/EP2019/076029 dated Apr. 8, 2021 (8 pages).
Taiwan Intellectual Property Office. Examination Report for corresponding Taiwan Application No. 108135227 dated Feb. 9, 2023 (33 pages).

* cited by examiner

AUTO-INJECTOR

CROSS-REFERENCE TO RELATED APPLICATIONS

The present application represents the United States National Stage of International Application No. PCT/EP2019/076029, filed Sep. 26, 2019, which relates to and claims priority to British Patent Application Serial No. GB 1815829.5, filed Sep. 28, 2018, both of which are incorporated herein by reference in their entirety.

TECHNICAL FIELD

The invention relates to auto-injectors for use with syringes. The invention may relate to, but need not be limited to, safety auto-injectors and/or auto-injectors for use with safety syringes.

BACKGROUND

Safety syringes typically include some form of safety mechanism to protect healthcare workers from a hypodermic needle of the syringe after it has been injected into a patient. Exemplary safety syringes may include a sheath for covering the needle after use of the syringe. Other exemplary syringes may cause the needle to retract within the barrel of the syringe.

Safety syringes may be broadly split into 'active' and 'passive' safety syringes. Active safety syringes typically require some action by a user of the syringe to engage the safety mechanism and/or deploy the sheath. Such action may be taken after removal of the needle from the patient, or may be taken during removal of the needle from the patient. Passive safety syringes typically engage the safety mechanism and/or deploy the sheath without any specific action by the user, that is, without any action other than that usually taken to use the syringe.

An auto-injector is a device for receiving a syringe and for driving a syringe plunger of the syringe into a barrel of the syringe without any force being applied by the user. Typically, an auto-injector includes a plunger driver and a drive spring that are arranged to provide a force to drive the syringe plunger into the barrel. The drive spring and plunger driver may be activated by operation of a button or other release mechanism on the auto-injector. A safety auto-injector may be one which includes a shroud that may be deployed to a position covering a needle of a syringe received within the auto-injector before and after use of the syringe. The shroud of the auto-injector may be deployed under a force applied by a shroud spring.

SUMMARY

According to an aspect of the invention there is provided an auto-injector for receiving and operating a syringe, the auto-injector comprising: a housing for receiving the syringe, the housing comprising a main body and a hinged door operable into an open position and a closed position, wherein the syringe is receivable within the housing when the hinged door is in the open position; at least one charging link connected between the main body and the hinged door, wherein the connection of the charging link to the main body and/or the connection of the charging link to the hinged door is a slidable connection configured to slide on opening and closing of the hinged door and configured to couple to the at least one drive spring for priming thereof on opening and/or closing of the hinged door, the at least one drive spring being configured on activation of the auto-injector to drive a plunger driver forward within the auto-injector to operate the syringe received within the auto-injector.

The hinged door provides a lever through which the user can gain a mechanical advantage when priming the drive spring.

Optionally, the syringe is receivable within the main body of the housing when the hinged door is in the open position.

Optionally, the connection of the charging link to the hinged door is fixed and the connection of the charging link to the main body is slidable.

Optionally, the at least one drive spring is positioned on the main body.

Optionally, the auto-injector further comprises a spring guide coupled to the at least one drive spring such that extension and contraction of the at least one drive spring follows a path of the guide.

Optionally, the charging link comprises a charging linkage configured to travel along the spring guide to provide the slidable connection of the charging link to the main body.

Optionally, the spring guide comprises a rod passing through the at least one drive spring and passing through an aperture in the charging linkage.

Optionally, the hinged door and the charging link are configured such that movement of the hinged door towards the open position causes the charging linkage to slide along the spring guide in a first direction to compress the at least one drive spring, priming it for operation of the syringe.

Optionally, the hinged door and the charging link are configured such that movement of the hinged door towards the closed position causes the charging linkage to slide along the spring guide in a second direction opposite the first direction.

Optionally, the auto-injector comprises a plurality of drive springs.

Optionally, the auto-injector comprises a plurality of charging links.

Optionally, one or more of the plurality of drive springs is configurable into one of an active state, in which the one or more drive springs contributes to driving the plunger driver forwards, and a passive state, in which the one or more drive springs does not contribute to driving the plunger driver forwards.

Optionally, the one or more drive springs is removable from the auto-injector to place it into the passive state.

Optionally, the plunger driver is connected to an end of the at least one drive spring and is drivable forwards under a force delivered by the at least one drive spring.

Optionally, the auto-injector further comprises a shroud at least partially covering and extending forwards beyond a forward end of a needle of the syringe when the syringe is fitted within the auto-injector and before use.

Optionally, the drive spring is retained in a primed state by a drive latch, and wherein the shroud is configured, on rearward movement thereof, to release the drive latch.

Optionally, the auto-injector comprises comprising a latch release arm extending rearwards from the shroud, wherein the drive latch comprises an angled surface, and the latch release arm comprises a drive release surface, and wherein, upon rearward movement of the shroud, the drive release surface rides along the angled surface of the drive latch to displace the drive latch laterally, thereby releasing the drive latch.

Optionally, the auto-injector comprises a sheath latch configured to halt forward movement of the plunger driver when the plunger reaches an end of its forward stroke.

Optionally, the shroud is biased in a forward direction by a shroud spring such that movement of the auto-injector away from an injection site allows forward movement of the shroud.

Optionally, the sheath latch comprises an angled surface and the latch release arm comprises a sheath release surface, and wherein, upon forward movement of the latch release arm, the sheath release surface rides along the angled surface of the sheath release latch, thereby releasing it.

Optionally, the driver spring is configured to drive the plunger driver further forwards after release of the sheath latch, and is further configured to deploy a sheath for at least partially covering the needle.

The auto-injector may be configured to receive and operate a safety syringe.

Optionally, the auto-injector comprises a damper configured to damp at least part of the forward and/or rearward motion of the plunger driver.

Optionally, the damper is configured to damp an initial portion of the forward motion of the plunger driver.

Optionally, the damper is configured to damp forward motion of the plunger driver during a full forward stroke of the plunger driver.

Optionally, the damper is further configured to damp rearward movement of the plunger driver.

Optionally, the damper is a rotary damper comprising a rack and pinion arrangement, wherein rotation of the pinion is damped.

Optionally, the shroud comprises a door portion and a main body portion, and wherein the door portion is slidably connected to the door and the main body portion is slidably connected to the main body, such that operation of the door towards the open position separates the door portion from the main portion.

Optionally, the door portion and the main body portion comprise keying features configured to engage when the door is in the closed position, such that forward and/or rearward movement of one of the door portion and the main body portion results in forward and/or rearward movement of the other of the door portion and the main body portion.

According to the invention in an aspect there is provided an auto-injector according to any disclosed herein further comprising a syringe or a safety syringe.

BRIEF DESCRIPTION OF THE DRAWINGS

Exemplary embodiments of the invention are disclosed herein with reference to the accompanying drawings, in which.

DETAILED DESCRIPTION

Generally, disclosed herein are exemplary methods and apparatus for auto-injectors and in some specific arrangements, safety auto-injectors. The term "auto-injector" is used herein and may be considered to encompass both an auto-injector and a safety auto-injector, as appropriate. The auto-injectors may be configured to receive and operate a standard syringe (i.e. not a safety syringe) and/or a safety syringe.

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use. Further, the term longitudinal is used to encompass a direction along or parallel to a longitudinal axis of the injection device.

Features of the exemplary arrangements disclosed herein are described as being "coupled" to other features. This term encompasses any coupling that results in the coupled features moving together in any direction, whether that be on a 1:1 basis or on some geared basis. The term "coupled" also encompasses any one of a connection between features, an abutment of one feature against another and an engagement of one feature with another, and such coupling may be direct or may be indirect, i.e. with a third feature therebetween.

Figures 1A, 1B:
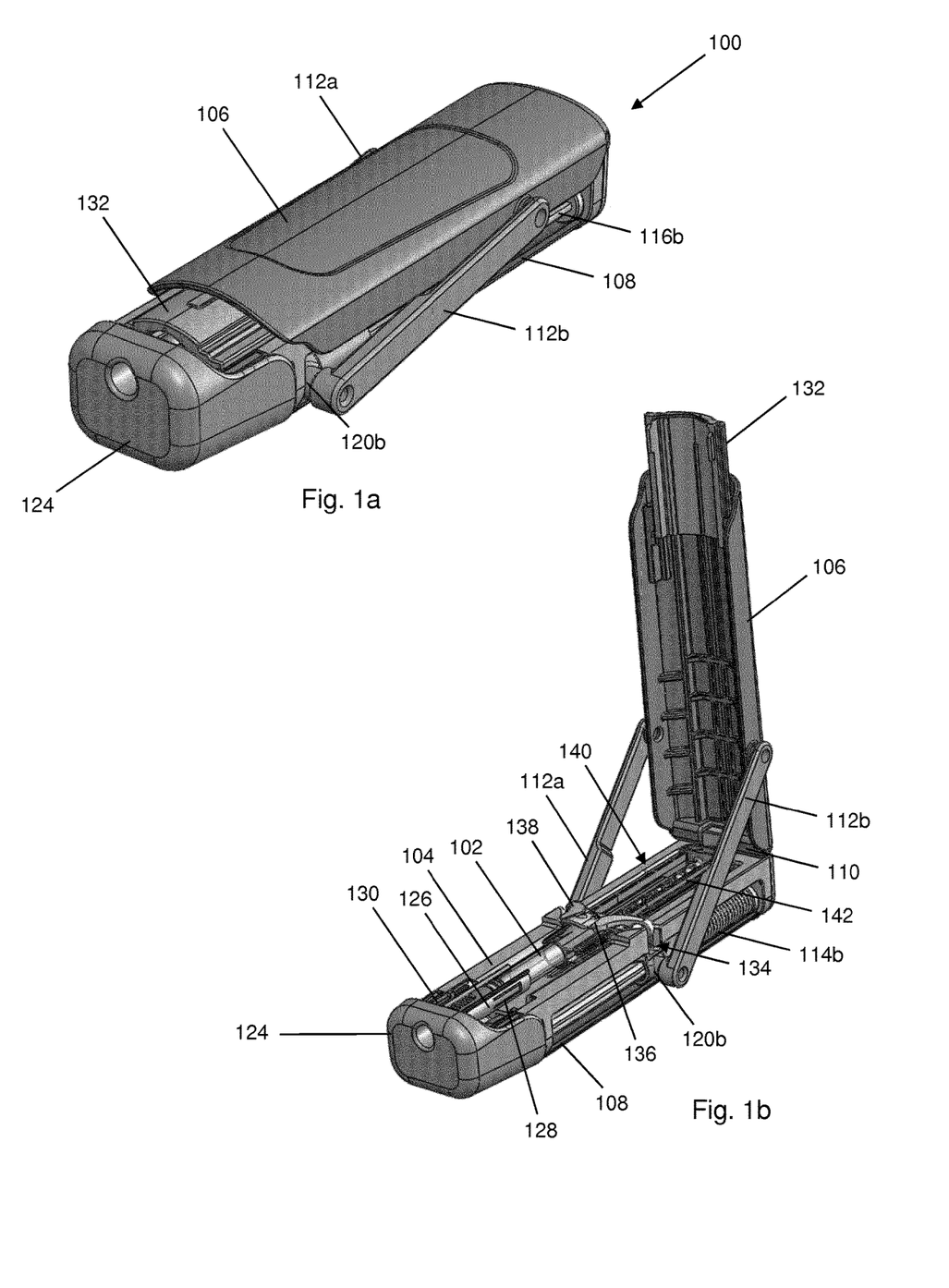
FIGS. 1a and 1b show perspective views of an auto-injector.

FIGS. 1a and 1b show an exemplary auto-injector 100 for receiving and operating a syringe 102. The auto-injector comprises a housing that further comprises a plurality of component parts. In the example of FIGS. 1a and 1b, the housing comprises a main body 104, a hinged door 106 (termed "door" herein) and in some exemplary arrangements, a rear body 108. FIG. 1a shows the auto-injector 100 with the door 106 in a closed position and FIG. 1b shows the auto-injector 100 with the door 106 in an open position. The door 106 is operable between these two positions. As can be seen, the syringe 102 may be received within the housing, and in this case specifically in the main body 104, when the door 106 is in the open position. The door 106 may comprise a hinged connection 110 with the main body 104.

Two charging links 112a, 112b connect the door 106 to the main body 104. Connections between the charging links 112a, 112b and the main body 104 and/or between the door 106 and the charging links 112a, 112b are slidable. This allows opening of the door 106 about the hinged connection 110. In the example shown in FIGS. 1a and 1b, the connection between the charging links 112a, 112b and the main body 104 is slidable.

The auto-injector 100 further comprises at least one drive spring and in the case of FIGS. 1a and 1b two drive springs 114a, 114b (drive spring 114a not shown in FIGS. 1a and 1b but located in a similar position to drive spring 114b on the opposite side of the auto-injector 100). The sliding connections of the charging links 112a, 112b to the main body 104 are configured to couple to the drive springs 114a, 114b to prime them by compression thereof on opening of the door 106. It will be apparent to the skilled person that other arrangements are possible such as priming the drive springs 114a, 114b on closing of the door 106.

The auto-injector 100 also comprises a spring guide 116a, 116b (spring guide 116a not shown in FIGS. 1a and 1b but located in a similar position to spring guide 116b on the opposite side of the auto-injector 100), which in the example shown in FIGS. 1a and 1b comprise rods. The rods have a cross-shaped cross section. The rods comprise a reaction surface 118a, 118b against which a rearward end of the drive springs 114a, 114b is placed. Extension of the drive springs 114a, 114b therefore produces a force acting in a forward direction.

The drive springs 114a, 114b are located about the rods such that the rods pass through an aperture defined by the drive springs 114a, 114b. In this way, extension and compression of the drive springs 114a, 114b follows the path defined by the spring guides 116a, 116b. The skilled person will appreciate that other forms of spring guide may be used.

The slidable connections of the charging links 112a, 112b may be provided by charging linkages 120a, 120b. The charging linkages 120a, 120b are rotationally connected to the charging links 112a, 112b and configured to slide along the spring guides 116a, 116b. In the case of FIGS. 1a and 1b, the charging linkages 120a, 120b comprise an aperture though which the spring guides 116a, 116b (e.g. rods) pass.

The auto-injector 100 also comprises two plunger drivers 122a, 122b, but these are not easily seen in FIGS. 1a and 1b and can best be seen in later figures, where their operation is fully described. Broadly, the plunger drivers 122a, 122b are connected or otherwise coupled to an end of the drive springs 114a, 114b such that extension of the drive springs 114a, 114b drives the plunger drivers 122a, 122b forwards. The plunger drivers 122a, 122b are arranged to contact a plunger of the syringe 102, thereby driving that forwards and operating the syringe 102.

An end cap 124 is fitted to a forward end of the auto-injector 100. The end cap 124 is removable before use of the auto-injector 100. The end cap 124 comprises a syringe receiving tray 126. The receiving tray 126 is configured to receive part of the barrel of the syringe 102 and a rigid needle shield (RNS) of the syringe 102. The syringe barrel and RNS are received within the receiving tray 126 by snap fit. The receiving tray also comprises an opposed pair of resiliently deformable prongs 128, which comprise catches. The catches are configured to hook onto the RNS during removal of the cap 124 to remove the RNS simultaneously with the cap 124.

The auto-injector 100 also comprises a shroud. In the exemplary arrangement of FIGS. 1a and 1b, the shroud comprises a main body portion 130 and a door portion 132. The main body portion 130 is slidably connected to the main body 104. The door portion 132 is slidably connected to the door 106. Therefore, and as shown in FIG. 1b, when the door 106 is in the open position, the shroud is split. This allows the syringe 102 to be loaded into the auto-injector 100 from the top without the need to thread the needle end of the syringe 102 through the shroud. The main body portion 130 and the door portion 132 also comprise keying features that are configured to interlock when the door 106 is in the closed position. This longitudinally couples the main body portion 130 to the door portion 132, which can then move together longitudinally. A shroud spring biases the shroud in a forward direction.

The main body 104 comprises one or more recessed areas that represent a "ghosted" impression of the syringe 102. For example, the main body may comprise a recess 134 for receiving a handle portion 136 and finger flanges 138 of the syringe 102. Further, the main body 104 may comprise a recess 140 for receiving an extended plunger assembly 142 of the syringe 102. The recess 140 may have a length that accounts for tolerances in bung position of prefilled syringes.

Figure 2A:
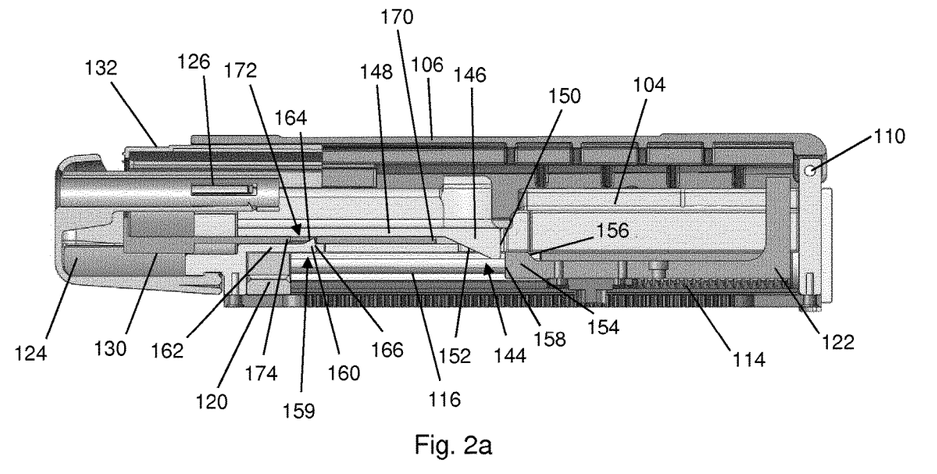
FIG. 2a shows a section through an auto-injector.
Figure 2B:
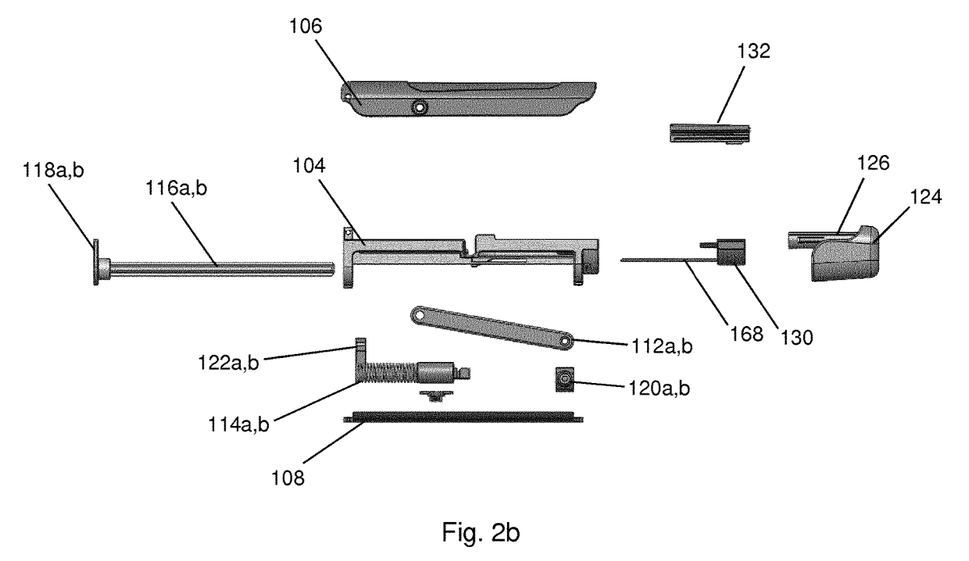
FIG. 2b shows an exploded view of an auto-injector.

FIGS. 2a and 2b show a section through the auto-injector 100 and an exploded view of the auto-injector 100 respectively. Many of the features already discussed in respect of FIGS. 1a and 1b are also shown in FIGS. 2a and 2b.

Referring to FIGS. 2a and 2b, the main body 104 comprises one or more driver latches 144. For the remainder of this part of the description, reference will be made to features on one side of a longitudinal axis of the auto-injector 100. However, the same features and associated description may be relevant to the opposite side of the longitudinal axis. The driver latch 144 is configured to prevent forward motion of the plunger driver 122. The driver latch 144 comprises a projection 146 that extends transverse to the longitudinal axis from a resiliently deformable arm 148. The projection 146 comprises a rearward facing latching surface 150 and a forward facing angled surface 152 extending laterally from a direction of the resiliently deformable arm 148. In a resting position of the resiliently deformable arm 148, the projection is in a path followed by the plunger driver 122 under the influence of the drive spring 114.

The plunger driver 122 comprises a projection 154 extending transverse to the longitudinal axis of the auto-injector. The projection 154 comprises a rearward facing angled surface 156 and a forward facing abutment surface 158. The abutment surface 158 is arranged to abut the latching surface 150 when the plunger driver 122 is retained by the driver latch 144.

The main body 104 also comprises a sheath latch 159 comprising a projection 160 projecting transverse to a resiliently deformable prong 162 and to a longitudinal axis of the auto-injector 100. The projection 160 comprises a rearward facing angled surface 164 and a forward facing latching surface 166. The shroud, and in the exemplary arrangement of FIGS. 1-2, the main body portion 130 of the shroud, comprises a rearward extending latch release arm 168. Rearward movement of the shroud and therefore the latch release arm 168 is configured to release the driver latch 144. In the example shown in the figures, this is achieved by a drive release surface 170. As explained below, the drive release surface 170 rides over the rearward facing angled surface of the driver latch 144 to release the driver latch 144 and allow forward movement of the plunger driver 122.

The latch release arm 168 also comprises an aperture or recess 172 in which the projection 160 of sheath latch 159 is received before operation of the auto-injector 100. This represents the resting position of the resiliently deformable prong 162. In the resting position of the prong 162, the projection 160 is out of the path of the plunger driver 122, which is therefore allowed to pass. A rear surface (or sheath release surface) 174 of the aperture 172 is configured to engage the latch by riding over the angled surface 164 of the projection 160 on rearward movement of the shroud. Subsequent forward movement of the shroud allows the projection 160 to re-enter the aperture 172 under force of the prong 162, thereby releasing the latch.

Figure 3A:
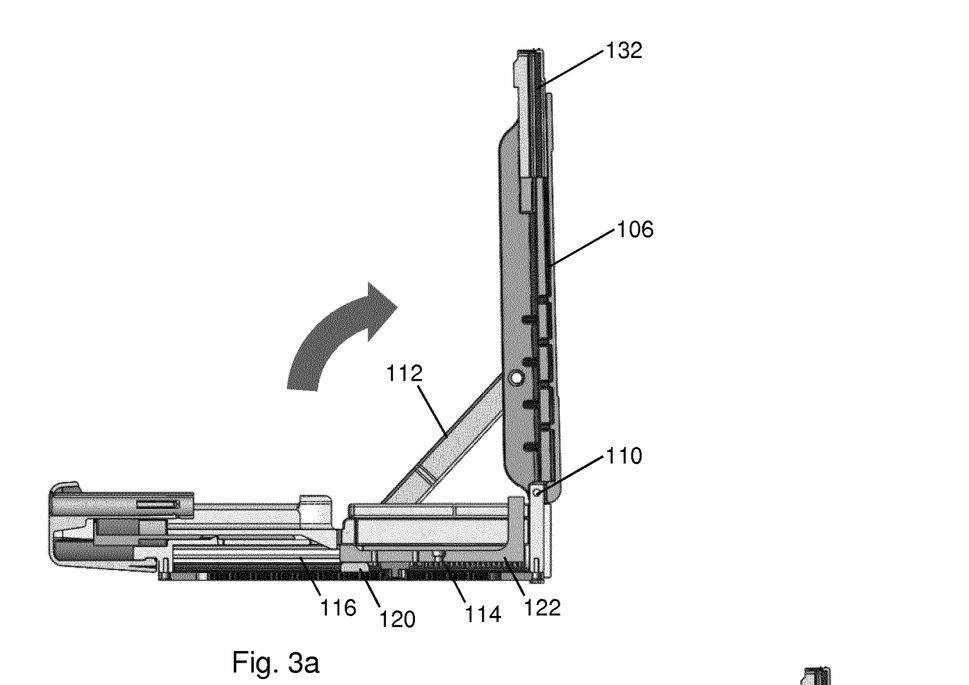
FIGS. 3a-3g show sections through an auto-injector at various stages of operation.

Operation of the auto-injector is now described with reference to FIGS. 3a-3g. In FIG. 3a, the hinged door 106 is opened about the hinged connection 110. This slides the charging linkage 120 of the charging link 112 along the spring guide 116. In cases where the door 106 is opened after operation of the device, the drive spring 114 will be extended along the spring guide 116 before opening. Therefore, the charging linkage 120 couples (in this case abuts) to the drive spring 114 during opening of the door 106. The lever action of the door 106 allows the user to gain a mechanical advantage in priming the drive spring 114. This may be a particular advantage when high force springs are used, for example when a drug to be delivered by the auto-injector has a high viscosity. In some examples, the viscosity of the drug may be in a range from 12 centipoise (cP) to 18 cP, in a range from 14 cP to 16 cP, or may be 15 cP. Further, the drug may need to be delivered through a 29 gauge thin wall needle, although other gauge needles may be used. This requires a relatively high spring force, for example 40 N to 50 N and may be 45 N, which a user may find difficult to prime.

During opening of the door 106, the charging linkage 120 compresses the drive spring 114 and moves the plunger driver 122 rearwards. The rearward facing angled surface 156 of the plunger driver 122 contacts the forward facing angled surface 152 of the driver latch 144 and displaces the projection 146 laterally allowing the plunger driver 122 to pass. After the plunger driver 122 has passed, the projection 146 springs back into the path of the plunger driver 122 under force of the resilient arm 148. The plunger driver 122 is therefore latched.

The door portion 132 moves with the door 106, thereby allowing the syringe 102 to be received into the auto-injector laterally without the need to thread the needle end through the shroud.

Figure 3B:
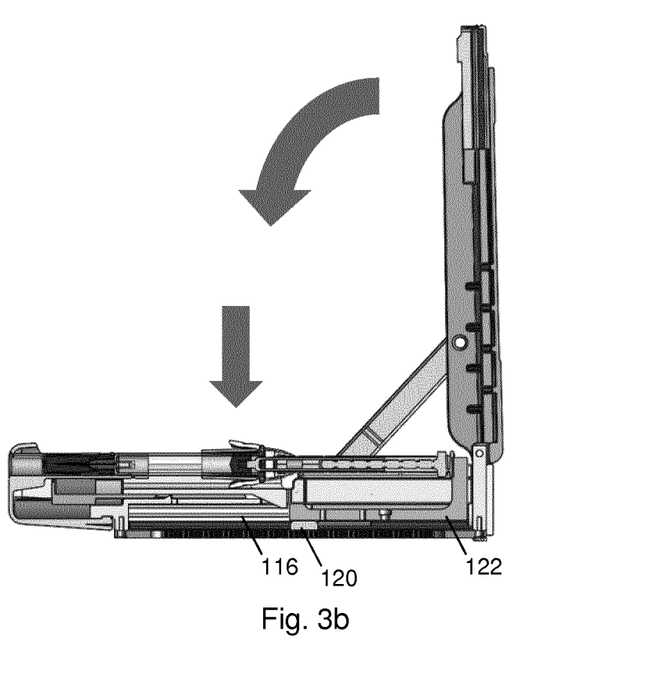

In FIG. 3b, the syringe 102 is inserted into the main body 104 using the ghosting recesses 134, 140 and the receiving tray 126. The door 106 is then closed about the hinged connection 110. The charging linkage 120 slides forwards along the spring guide 116. The plunger driver 122 is retained by the driver latch 144 and the drive spring 114 does not expand along the spring guide 116. There is therefore room on the spring guide 116 into which the drive spring 114 can expand on operation of the auto-injector 100. The door portion 132 of the shroud connects to the main body portion 130 of the shroud via the keying features such that the two are longitudinally coupled or connected.

Figure 3C:
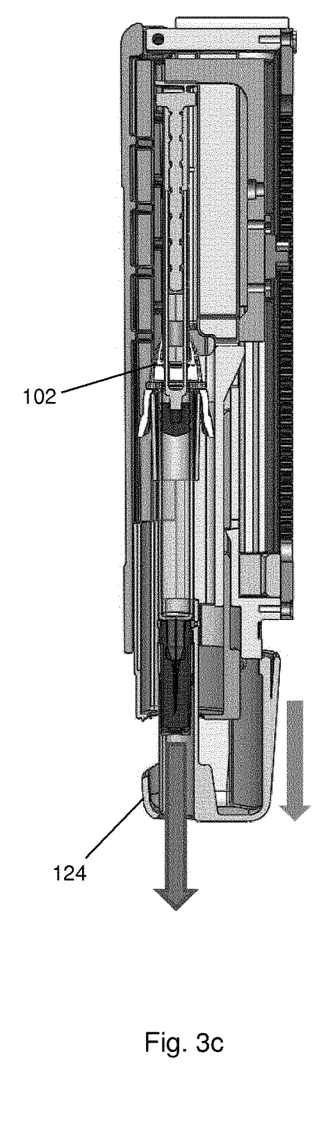

FIG. 3c shows the cap 124 being removed. The deformable prongs 128 of the receiving tray 126 catch on the RNS of the syringe 102, which is therefore also removed. The cap 124 comprises an aperture through which the RNS drops after removal from the needle.

Figure 3D:
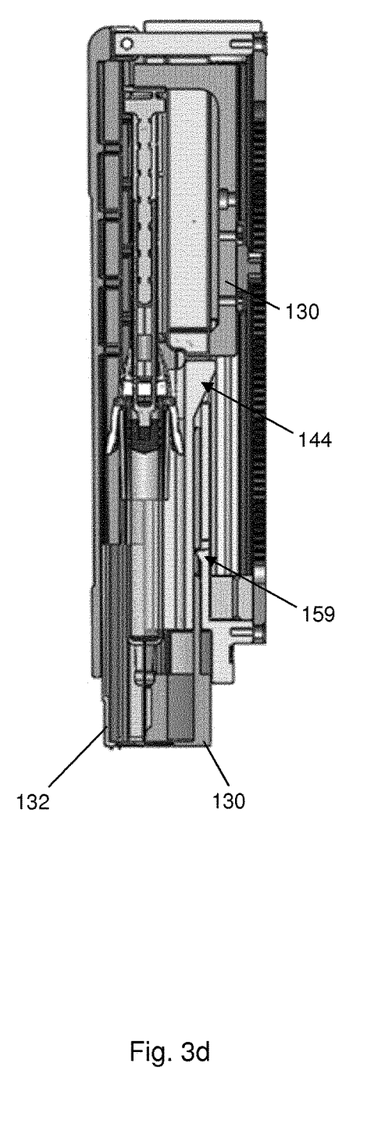

As can be seen in FIG. 3d, the main body portion 130 and the door portion 132 of the shroud surround the needle and extend beyond the forward end of the needle, which is therefore shielded. The shroud is biased in a forward direction under force of a shroud spring. The driver latch 144 is engaged and therefore is in the path of the plunger driver 122. Further, the sheath latch 159 is received with the aperture 172 of the latch release arm 168 and is out of the path of the plunger driver 122.

Figure 3E:
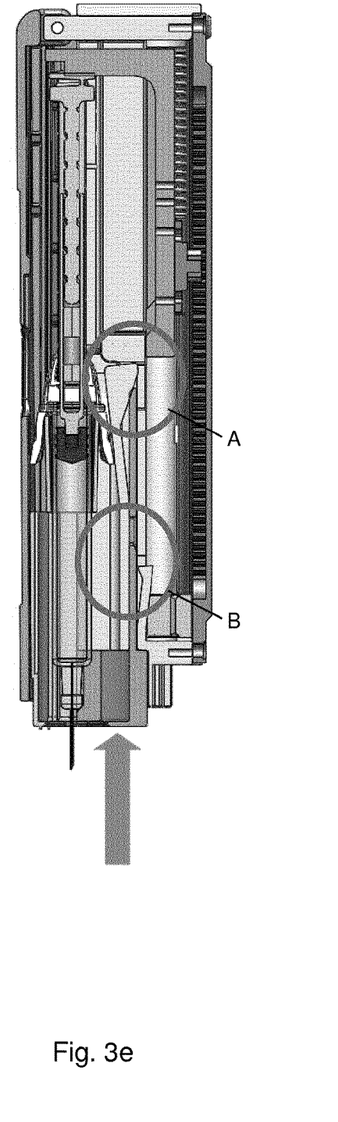
Figure 3F:
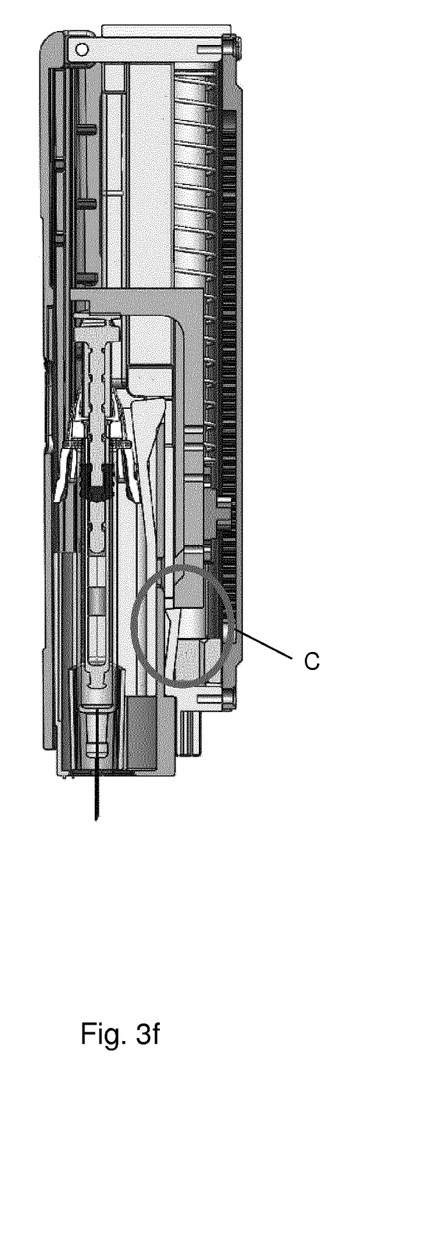

In FIG. 3e the shroud is pushed rearwards into the auto-injector 100. This may be done by a user pressing the shroud against an injection site. This action exposes the needle, which enters the injection site. In other arrangements, the syringe 102 may be moved forward within a syringe carrier under force of a spring. In such arrangements, rearward movement of the shroud (or indeed the depression of a button) may release the spring to drive the syringe carrier forwards for needle insertion.

The forward facing drive release surface 170 of the latch release arm 168 rides over the rearward facing angled surface of the projection 146 of the driver latch 144. This displaces the projection 146 laterally out of the path of the plunger driver 122 (to the left in FIG. 3e). This action can be seen in the circle A of FIG. 3e. Also, rearward movement of the shroud causes the sheath release surface 174 of the aperture 172 in the latch release arm 168 rides over the rearward facing angled surface 164 of the projection 160 of the sheath latch 159. This displaces the projection 160 laterally into the path of the plunger driver 122 (to the right in FIG. 3e). This action can be seen in the circle B.

Disengagement of the driver latch 144 releases the drive spring 114, which drives the plunger driver forwards and thereby drives the plunger of the syringe 102 into the barrel. This forces the bung further into the barrel and dispenses the drug (or other substance) from the syringe 102. In some arrangements, movement of the plunger driver 122 may be damped, in particular during an initial phase of a forward stroke. This is described below in more detail.

The plunger driver 122 is driven forwards until it reaches the sheath latch 159, which is now engaged and in the path of the plunger driver 122. The sheath latch 159 therefore halts progress of the plunger driver 122. The sheath latch 159 may be positioned such that the plunger 122 driver is halted at a point on the forward stroke at which the full dose of drug has been delivered from the barrel or at a point afterwards. The exemplary arrangement shown in the figures is configured for use with a safety syringe in which further movement of a plunger after full dose delivery deploys a sheath to protect the needle after use of the syringe 102. Therefore, halting forward motion of the plunger driver 122 prevents deployment of the sheath. It will be appreciated that sheaths of safety syringes may also be deployed under force of a separate spring that may be released by a sheath release mechanism. Such a mechanism may be released by forward movement of the plunger (or plunger driver 122) after full dose delivery. Such arrangements are encompassed within embodiments disclosed herein.

Figure 3G:
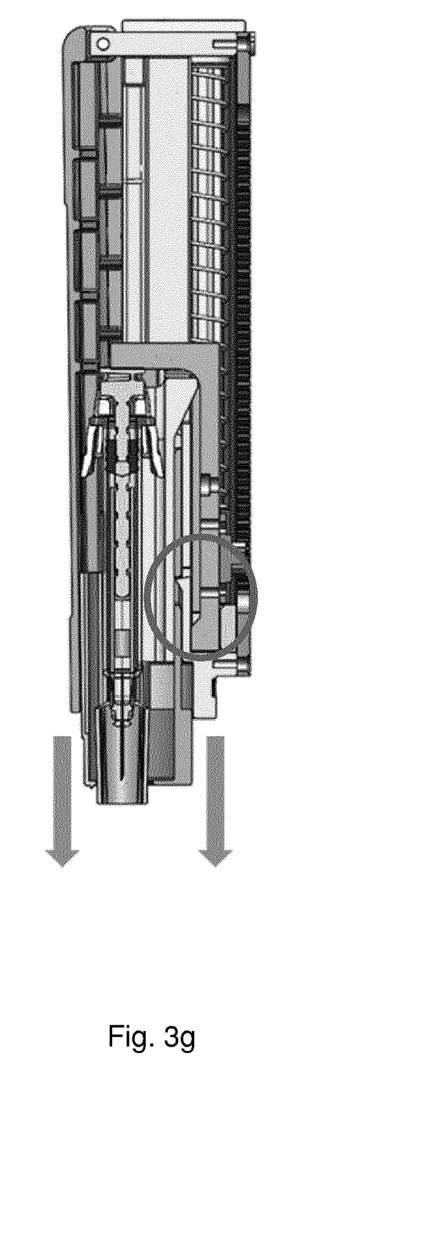

After full dose delivery, the user lifts the auto-injector away from the injection site. The shroud is therefore urged forwards under the force of the shroud spring, which is shown in FIG. 3g. Forward movement of the shroud causes forward movement of the latch release arm 168 until the aperture 172 is longitudinally aligned with the projection 160. The projection 160 therefore enters the aperture 172 under force of the prong 162. This disengages the sheath latch 159 and moves the projection 160 out of the path of the plunger driver 122 allowing forward movement thereof. Further forward movement of the plunger driver 122 causes further forward movement of the plunger of the auto-injector 100, thereby deploying the sheath.

The door 106 can now be opened, priming the drive spring 114 again and allowing removal of the sheathed safety syringe 102.

In some arrangements, a plurality of drive springs 114 may be located on the auto-injector 100. One or more of the plurality of drive springs 114 may be configured to be in an active or a passive state. That is, one or more of the drive springs 114 may be configured either to contribute to driving the plunger driver 122 forwards or not to contribute to driving the plunger driver 122 forwards. Configuration may comprise removing one or more of the drive springs 114 from the auto-injector 100. This may be done during assembly of the auto-injector 100. In other arrangements, a setting on the auto-injector may configure the one or more drive springs 114. For example, one of the charging links 112 may be disconnected from the door 106.

Figure 4:
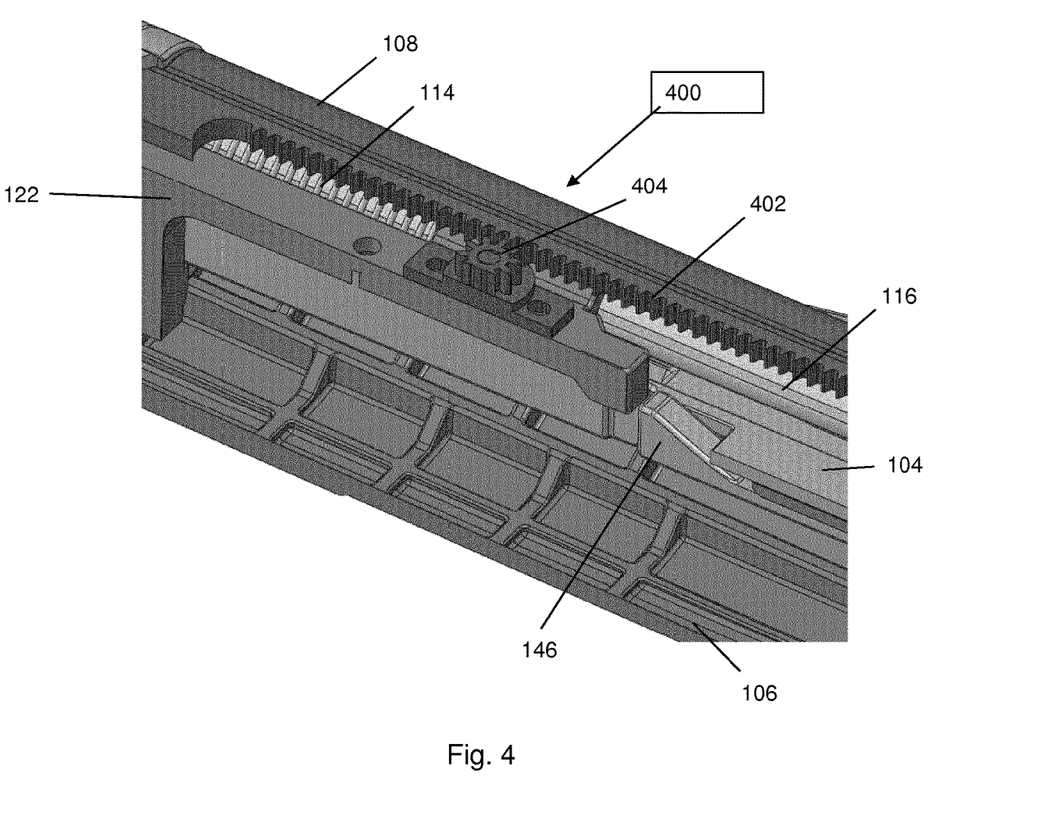
FIG. 4 shows an exemplary damper for an auto-injector.

FIG. 4 shows an exemplary damper 400 fitted to the auto-injector 100. The damper 400 may be configured to damp forward and/or rearward motion of the plunger driver 122. In one example, the damper 400 is configured to damp at least an initial phase of the forward motion of the plunger driver 122. This initial phase may be up to 15 mm, up to 10 mm or up to 5 mm. In this way, tolerances in bung position may be accounted for. Bung position may affect the overall length of the auto-injector 100 and/or the amount of travel of the plunger driver 122 before the plunger is in contact with the bung and the bung is in contact with the drug within the barrel. During this travel, the spring force may cause rapid acceleration of the plunger, which may then cause damage to the syringe or discomfort to the recipient of the injection when contact between the three elements is made. Damping of the forward motion of the plunger driver 122 reduces or overcomes the risk of this.

The damper 400 may also be configured to operate over more of the forward travel of the plunger driver 122, and in some arrangement may operate over the full forward travel of the plunger driver. This reduces shock effects and wear on the components of the auto-injector, increasing their life.

Further, the damper 400 may damp rearward travel of the plunger driver 122. This prevents the door 106 snapping shut if released during opening and priming of the drive spring 114.

In FIG. 4, the exemplary damper 400 comprises a rack 402 and pinion 404 arrangement. The pinion 404 is connected to the plunger driver and travels along the rack 402 with movement of the plunger driver 122 forwards or backwards. The pinion 404 is configured to have damped rotation in one or both direction for damping travel of the plunger driver 122.

Figure 5:
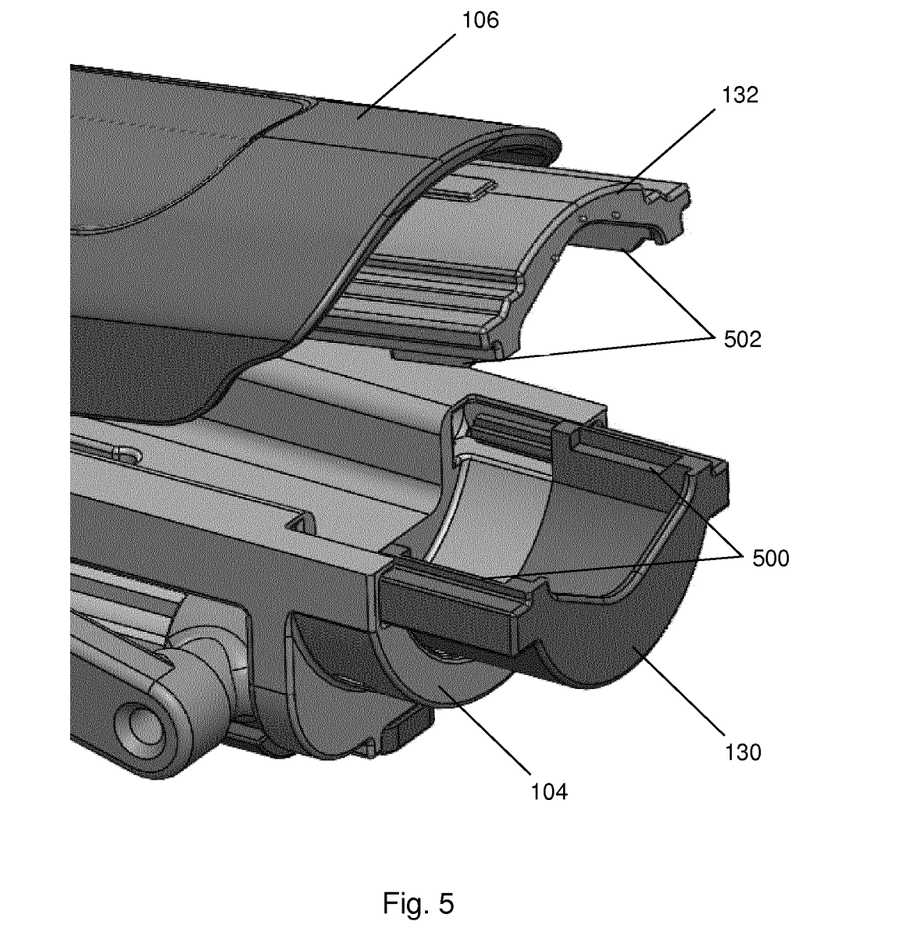
FIG. 5 shows exemplary keying features for a main body portion and a door portion of a shroud for an auto-injector.

FIG. 5 shows the main body portion 130 and the door portion 132 of the shroud. The keying features of the main body portion 130 comprise keying recesses 500. The keying features of the door portion 132 comprise keying projections 502. The keying projections 502 are configured to enter the keying recesses 500 when the door 106 is in the closed position, thereby longitudinally coupling or connecting the main body portion 130 to the door portion 132. The skilled person will appreciate that other arrangements are possible for such connection and, in particular, the keying recesses may be located on the door portion and the keying projections may be located on the main body portion.

The skilled person will be able to envisage other assemblies, auto-injectors and features thereof without departing from the scope of the appended claims. In particular, it is noted that one or more features included in one or more drawings may be integrated into auto-injectors shown in other drawings, as will be appreciated by the skilled person.

The invention claimed is:

1. An auto-injector for receiving and operating a syringe, the auto-injector comprising:
   a housing for receiving the syringe, the housing comprising a main body and a hinged door operable into an open position and a closed position, wherein the syringe is receivable within the housing when the hinged door is in the open position;
   at least one charging link connected between the main body and the hinged door, wherein a connection of the at least one charging link to the main body and/or a connection of the at least one charging link to the hinged door is a slidable connection configured to slide on opening of the hinged door and closing of the hinged door and configured to couple to at least one drive spring for priming of the at least one drive spring on the opening of the hinged door and/or the closing of the hinged door,
   the at least one drive spring being configured on activation of the auto-injector to drive a plunger driver forward within the auto-injector to operate the syringe received within the auto-injector;
   a shroud at least partially covering and extending forwards beyond a forward end of a needle of the syringe when the syringe is fitted within the auto-injector and before use of the syringe, wherein the shroud comprises a door portion and a main body portion, wherein the door portion is slidably connected to the hinged door and the main body portion is slidably connected to the main body, such that operation of the hinged door towards the open position separates the door portion from the main body portion, and wherein the door portion and the main body portion comprise keying features configured to engage when the hinged door is in the closed position such that the door portion and the main body portion move together in a forward direction and a rearward direction when the hinged door is in the closed position; and
   a drive latch, wherein the at least one drive spring is retained in a primed state after the opening of the hinged door and/or the closing of the hinged door, by the drive latch, and wherein the shroud is configured, on rearward movement of the shroud, to release the drive latch such that the at least one drive spring drives the plunger driver forward within the auto-injector.

2. The auto-injector according to claim 1, wherein the syringe is receivable within the main body of the housing when the hinged door is in the open position.

3. The auto-injector according to claim 1, wherein the connection of the at least one charging link to the hinged door is fixed and the connection of the at least one charging link to the main body is slidable.

4. The auto-injector according to claim 3, wherein the at least one drive spring is positioned on the main body.

5. The auto-injector according to claim 4, further comprising a spring guide coupled to the at least one drive spring such that extension of the at least one drive spring and contraction of the at least one drive spring follows a path of the spring guide.

6. The auto-injector according to claim 5, wherein the at least one charging link comprises a charging linkage configured to travel along the spring guide to provide the connection of the at least one charging link to the main body that is slidable.

7. The auto-injector according to claim 6, wherein the spring guide comprises a rod passing through the at least one drive spring and passing through an aperture in the charging linkage.

8. The auto-injector according to claim 6, wherein the hinged door and the at least one charging link are configured such that movement of the hinged door towards the open position causes the charging linkage to slide along the spring guide in a first direction to compress the at least one drive spring, priming the at least one drive spring for the operation of the syringe.

9. The auto-injector according to claim 8, wherein the hinged door and the at least one charging link are configured such that movement of the hinged door towards the closed position causes the charging linkage to slide along the spring guide in a second direction opposite the first direction.

10. The auto-injector according to claim 1,
   wherein the at least one drive spring is a plurality of drive springs,
   wherein the at least one charging link is a plurality of charging links, and
   wherein one or more drive springs of the plurality of drive springs is configurable into one of an active state, in which the one or more drive springs of the plurality of drive springs contributes to the driving of the plunger driver forwards, and a passive state, in which the one or more drive springs of the plurality of drive springs does not contribute to the driving of the plunger driver forwards, and wherein the one or more drive springs of the plurality of drive springs is removable from the auto-injector to place the one or more drive springs of the plurality of drive springs into the passive state.

11. The auto-injector according to claim 1, wherein the plunger driver is connected to an end of the at least one drive spring and is drivable forwards under a force delivered by the at least one drive spring.

12. The auto-injector according to claim 1, further comprising a latch release arm extending rearwards from the shroud, wherein the drive latch comprises an angled surface, and the latch release arm comprises a drive release surface, and wherein, upon the rearward movement of the shroud, the drive release surface rides along the angled surface of the drive latch to displace the drive latch laterally, thereby releasing the drive latch.

13. The auto-injector according to claim 1, further comprising a sheath latch configured to halt forward movement of the plunger driver when the plunger driver reaches an end of a forward stroke.

14. The auto-injector according to claim 13, wherein the shroud is biased in the forward direction by a shroud spring such that movement of the auto-injector away from an injection site allows forward movement of the shroud, and wherein the sheath latch comprises an angled surface and a latch release arm comprises a sheath release surface, and wherein, upon forward movement of the latch release arm, the sheath release surface rides along the angled surface of the sheath latch, thereby releasing the sheath latch.

15. The auto-injector according to claim 14, wherein the at least one drive spring is configured to drive the plunger driver further forwards after the release of the sheath latch, and is further configured to deploy a sheath for at least partially covering the needle.

16. The auto-injector according to claim 1, wherein the syringe is a safety syringe.

17. The auto-injector according to claim 1, further comprising a damper configured to damp at least part of a forward motion of the plunger driver and/or a rearward motion of the plunger driver.

18. The auto-injector according to claim 17, wherein the damper is configured to damp an initial portion of the forward motion of the plunger driver, wherein the damper is configured to damp the forward motion of the plunger driver during a full forward stroke of the plunger driver, wherein the damper is further configured to damp the rearward motion of the plunger driver, and wherein the damper is a rotary damper comprising a rack and a pinion, wherein rotation of the pinion is damped.

19. The auto-injector according to claim 1, further comprising the syringe received within the housing.

* * * * *